(12) United States Patent
Galley et al.

(10) Patent No.: US 8,323,344 B2
(45) Date of Patent: Dec. 4, 2012

(54) EXPANDABLE SPINAL PROSTHESIS

(75) Inventors: Geoffrey Harrison Galley, London (GB); James Bernard Allibone, Herts (GB); Mohammed Hamza Hilali Noordeen, London (GB); Benjamin Anthony Taylor, Herts (GB); Stewart Kenneth Tucker, London (GB)

(73) Assignee: EBI, LLC, Parsippany, NJ (US)

(*) Notice: Subject to any disclaimer, the term of this patent is extended or adjusted under 35 U.S.C. 154(b) by 560 days.

(21) Appl. No.: 12/294,357

(22) PCT Filed: Mar. 23, 2007

(86) PCT No.: PCT/US2007/007206
§ 371 (c)(1),
(2), (4) Date: Dec. 29, 2009

(87) PCT Pub. No.: WO2007/111979
PCT Pub. Date: Oct. 4, 2007

(65) Prior Publication Data
US 2010/0174373 A1     Jul. 8, 2010

(30) Foreign Application Priority Data
Mar. 24, 2006   (GB) .................................. 0605960.4

(51) Int. Cl.
*A61F 2/44* (2006.01)
(52) U.S. Cl. .................................... 623/17.16; 254/122
(58) Field of Classification Search .... 623/17.13–17.16; 606/90; 411/340–346; 254/122, 124, 126, 254/130, 131
See application file for complete search history.

(56) References Cited

U.S. PATENT DOCUMENTS

| | | | | |
|---|---|---|---|---|
| 3,976,281 A | * | 8/1976 | Adamson, Jr. ................ | 254/126 |
| 4,493,478 A | * | 1/1985 | Fortgens ....................... | 254/126 |
| 4,713,003 A | | 12/1987 | Symington et al. | |
| 4,720,082 A | * | 1/1988 | Yang ............................. | 254/126 |
| 5,364,072 A | * | 11/1994 | Engel ............................ | 254/126 |
| 5,553,919 A | | 9/1996 | Dennis | |

(Continued)

FOREIGN PATENT DOCUMENTS

EP       1994901      11/2008

(Continued)

OTHER PUBLICATIONS

International National Search Report for PCT Application No. PCT/US07/07206 dated Mar. 4, 2008 (3 pages).

*Primary Examiner* — Alvin Stewart
*Assistant Examiner* — Stuart S Bray
(74) *Attorney, Agent, or Firm* — Harness, Dickey

(57) ABSTRACT

A device is disclosed for insertion in the human or animal body in order to increase the spacing between adjacent spinous processes of the spinal column. The device comprises a plurality of shaped members which are pivotally joined to each other and arranged around a central screwed rod which is supported by a collar at one end and a threaded collar at the opposite end said collar and collar being located within the pivoting axis of the adjacent members forming each end of the device. Following insertion in the body and positioning between adjacent spinous processes the device may be deployed by rotation of the central screwed rod in order to achieve the desired separation of adjacent spinous processes while at the same time providing a secure location of the device in the deployed condition.

12 Claims, 3 Drawing Sheets

U.S. PATENT DOCUMENTS

| | | | |
|---|---|---|---|
| 5,678,804 A * | 10/1997 | Lintelman et al. | 254/131 |
| 6,070,856 A * | 6/2000 | Alten | 254/126 |
| 6,090,112 A | 7/2000 | Zucherman et al. | |
| 6,179,873 B1 | 1/2001 | Zientek | |
| 6,494,883 B1 | 12/2002 | Ferree | |
| 7,763,077 B2 * | 7/2010 | Friedman et al. | 623/17.16 |
| 7,875,078 B2 * | 1/2011 | Wysocki et al. | 623/17.15 |
| 2003/0144737 A1 | 7/2003 | Sherman | |
| 2003/0236520 A1 * | 12/2003 | Lim et al. | 606/61 |
| 2005/0261769 A1 | 11/2005 | Moskowitz et al. | |
| 2006/0184247 A1 | 8/2006 | Edidin et al. | |
| 2006/0184248 A1 | 8/2006 | Edidin et al. | |
| 2006/0265066 A1 | 11/2006 | Zucherman et al. | |
| 2007/0032790 A1 | 2/2007 | Aschmann et al. | |
| 2007/0043361 A1 | 2/2007 | Malandain et al. | |
| 2007/0043362 A1 | 2/2007 | Malandain et al. | |
| 2007/0049934 A1 | 3/2007 | Edidin et al. | |
| 2007/0049935 A1 | 3/2007 | Edidin et al. | |
| 2007/0055237 A1 | 3/2007 | Edidin et al. | |
| 2007/0161992 A1 | 7/2007 | Kwak et al. | |
| 2007/0225706 A1 | 9/2007 | Clark et al. | |
| 2007/0233076 A1 | 10/2007 | Trieu | |
| 2007/0260245 A1 | 11/2007 | Malandain et al. | |
| 2007/0265623 A1 | 11/2007 | Malandain et al. | |
| 2007/0276372 A1 | 11/2007 | Malandain et al. | |
| 2007/0299526 A1 * | 12/2007 | Malandain | 623/17.16 |
| 2008/0033559 A1 | 2/2008 | Zucherman et al. | |
| 2008/0033560 A1 | 2/2008 | Zucherman et al. | |
| 2008/0039944 A1 | 2/2008 | Malandain et al. | |
| 2008/0046086 A1 | 2/2008 | Zucherman et al. | |
| 2008/0051893 A1 | 2/2008 | Malandain et al. | |
| 2008/0051895 A1 | 2/2008 | Malandain et al. | |
| 2008/0051898 A1 | 2/2008 | Zucherman et al. | |
| 2008/0051899 A1 | 2/2008 | Zucherman et al. | |
| 2008/0051906 A1 | 2/2008 | Malandain et al. | |
| 2008/0058934 A1 | 3/2008 | Malandain et al. | |
| 2008/0058937 A1 | 3/2008 | Malandain et al. | |
| 2008/0065214 A1 | 3/2008 | Zucherman et al. | |
| 2008/0071376 A1 | 3/2008 | Kohm et al. | |
| 2008/0086212 A1 | 4/2008 | Zucherman et al. | |
| 2008/0108990 A1 * | 5/2008 | Mitchell et al. | 606/61 |
| 2008/0114367 A1 * | 5/2008 | Meyer | 606/90 |
| 2008/0147192 A1 | 6/2008 | Edidin et al. | |
| 2008/0161818 A1 | 7/2008 | Kloss et al. | |
| 2008/0281423 A1 | 11/2008 | Sheffer et al. | |
| 2009/0012528 A1 | 1/2009 | Aschmann et al. | |

FOREIGN PATENT DOCUMENTS

| | | |
|---|---|---|
| WO | 2006045094 A2 | 4/2006 |
| WO | 2007110604 A1 | 10/2007 |
| WO | 2008136877 | 11/2008 |

* cited by examiner

EXPANDABLE SPINAL PROSTHESIS

CROSS REFERENCE TO RELATED APPLICATIONS

This application is a 371 U.S. National Stage of International Application No. PCT/US2007/007206, filed Mar. 23, 2007. This application claims the benefit of Foreign Patent Application No. GB 0605960.4, filed Mar. 24, 2006. The disclosures of the above applications are expressly incorporated herein by reference.

FIELD

This invention relates to the insertion of one or more spacing means in the human vertebral column and is a further improved means of provision and insertion of such spacing means.

BACKGROUND

In another application by the same inventors (0502872.5), an improved means of achieving the desired separation of adjacent vertebral processes is provided in the form of a tapered segmented screw-like device which can be deployed using minimally invasive surgical techniques known to those skilled in the surgical art. It is the object of the present invention to provide a further improved means of separating the adjacent vertebral processes which has a minimal cross-sectional profile during insertion so that both the time taken for the surgical procedure, and the trauma caused by the procedure, are further reduced. In addition, the manufacture of the present invention is less complex and therefore less costly than that of the device described in the above mentioned previous application.

SUMMARY

The present invention consists of a plurality of shaped members which are pivotally joined to each other and arranged around a central screwed rod which is supported by a collar at one end and a threaded collar at the opposite end said collar and collar being located within the pivoting axis of the adjacent members forming each end of the device.

DRAWINGS

The drawings described herein are for illustrative purposes only of selected embodiments and not all possible implementations, and are not intended to limit the scope of the present disclosure.

FIG. 3a shows a collar and spring of the device of FIG. 1a; and

Corresponding reference numerals indicate corresponding parts throughout the several views of the drawings.

DETAILED DESCRIPTION

Figure 1A:
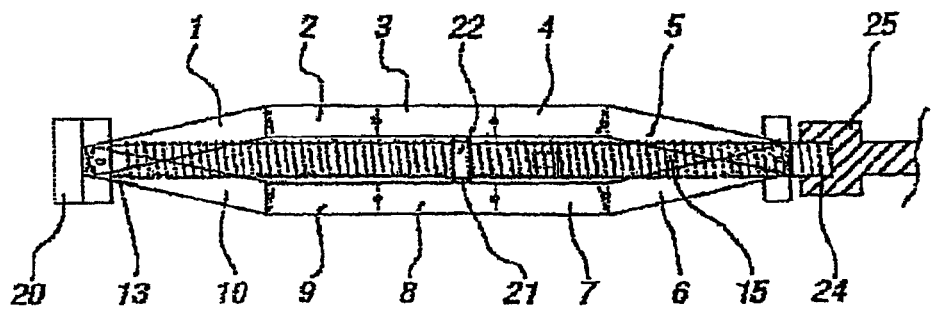
FIG. 1a represents a longitudinal cross sectional schematic view of a device in accordance with the principles of the present disclosure in a pre-insertion or extended condition.
Figure 1B:
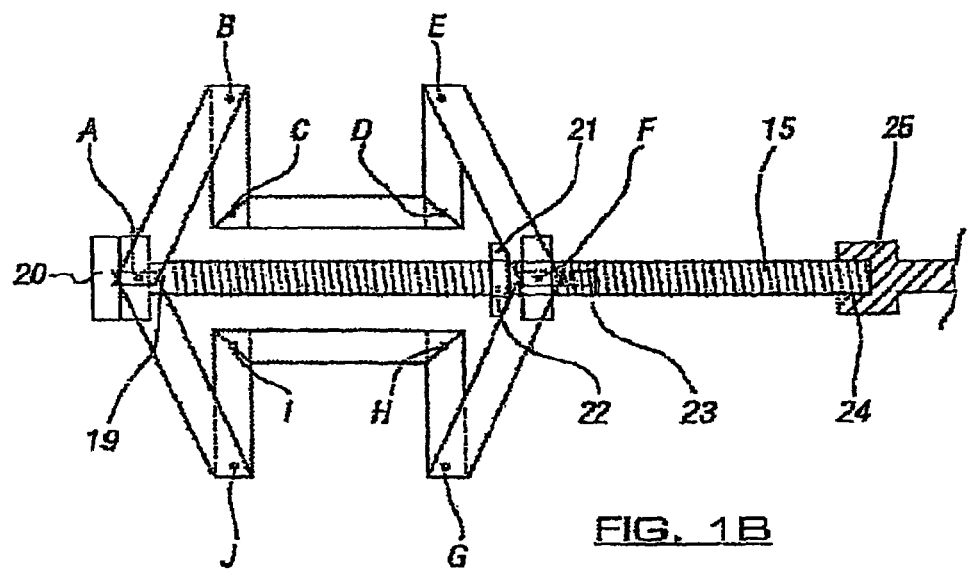
FIG. 1b represents a longitudinal cross sectional schematic view of the device of FIG. 1a in a compressed condition following insertion between adjacent spinous processes of adjacent vertebrae.
Figure 1C:
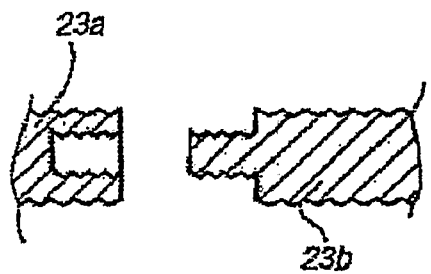
FIG. 1c shows a detail of a junction of the device of FIG. 1a in a central screwed rod.
Figure 2:
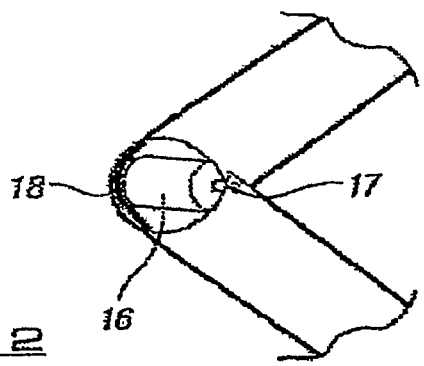
FIG. 2 represents an orthogonal view of a junction between two adjacent members such as occurs at points B, C, D, E, G, H, I and J shown in FIG. 1b.
Figure 3A:
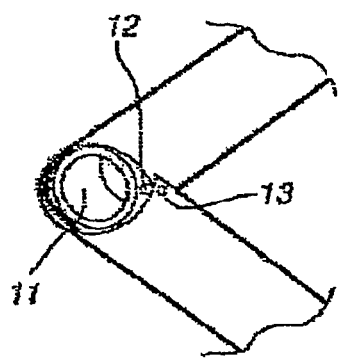
Figure 3B:
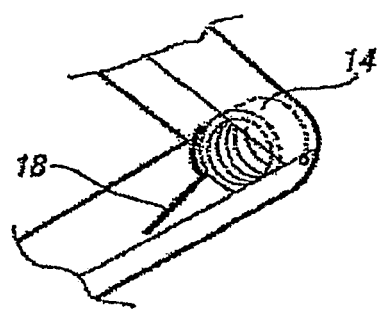
FIG. 3b shows positioning of a threaded collar and spring of the device of FIG 1a within member of the device at the right-hand end of the device (point F on FIG. 1b).

An embodiment of the device is now described with reference to FIGS. 1a, 1b, 1c, 2, 3a and 3b attached. FIG. 1a represents a longitudinal cross sectional schematic view of the device in its pre-insertion or extended condition and FIG. 1b represents the same view in the compressed condition following insertion between the adjacent spinous processes of adjacent vertebrae. FIG. 1c shows a detail of the junction (23) in the central screwed rod (15) shown in FIGS. 1a and 1b. FIG. 2 represents an orthogonal view of a junction between two adjacent members such as occurs at points B, C, D, E, G, H, I and J shown on FIG. 1b. FIG. 3a shows the manner in which, the collar (11) and spring (18) referred to in the description are positioned between the members at the left hand end of the device (point A on FIG. 1b) while FIG. 3b shows the positioning of the threaded collar (14) and spring (18) within the members at the right hand end of the device (point F on FIG. 1b).

The ten members of the device shown as items 1-10 in FIG. 1a are pivotally joined at locations A to J in FIG. 1b providing for an increase or decrease in the angle contained between adjacent members as may be required for the proper functioning of the device. As will be apparent from inspection of FIGS. 2, 3a and 3b, the cross sectional dimensions of alternate adjacent members differ so that at each junction between said adjacent members one member may fit inside the other member. The pivotal means provided at point A in FIG. 1b is shown in more detail in FIG. 3A and consists of a circular collar 11 provided at diametrically opposite sides with short rod like projections 12 which together provide a pivoting axle which passes through a small aperture 13 in either side of each of the two members located around said point A. The pivotal means provided at point F of FIG. 1b is shown in more detail; in FIG. 3B. Said pivotal means is similar to that provided at point A with the exception that said collar is replaced by a threaded collar 14 through which a centrally located screwed rod shown at 15 on FIGS. 1a and 1b may be advanced or withdrawn. The pivotal means provided at all other junctions between adjacent members is shown in FIG. 2 and comprises a cylindrical axle-pin 16 provided with concentric sections of different diameters to facilitate its retention within the small holes 17 provided in the respective adjacent members. A wire spring 18 is provided at each pivotal joint between said adjacent members so as to tension said members into an appropriate position during compression and extension of the device of the invention in the manner described herein.

The screwed rod 15 in FIGS. 1a and 1b is provided at its left hand end with an unthreaded portion 19 to facilitate its rotating motion in the collar (11 in FIG. 3a) and a terminating cap 20 to prevent its complete withdrawal through said collar. Said screwed rod is further provided with a stop nut 21 in FIGS. 1a and 1b which is fixed at a permanent location on screwed rod 15 by means of a transfixing pin (22 in FIG. 1a) or other suitable means.

Said screwed rod is provided at point 23, shown to the right of stop nut 21 in FIG. 1b, with a joint (shown in further detail in FIG. 1c) which facilitates removal of the section of said screwed rod to the right of said joint. Detachment of one portion of said screwed rod from the other portion may be advantageously provided by means of a threaded portion of reduced diameter on one section of said screwed rod shown in FIG. 1c at 23a which enters a matching socket 23b on the other section. Said screwed rod is further provided at the right hand end with a shaped portion 24 for attachment of a driving tool which may be in the form of a catheter as shown at 25 on FIGS. 1a and 1b.

In operation said driving tool is attached to said shaped portion (24) of said screwed rod (15) which is rotated so as to render the device into its expanded or stretched condition as shown in FIG. 1a. The device with driving tool attached is now advanced down a previously inserted canula into the body of the patient and positioned between the spinous processes which require separation. The driving tool is then used to rotate said screwed rod in an anti-clockwise direction thereby compressing the device of the invention into the condition shown in FIG. 1b. At this point the stop nut 21 engages with the threaded collar 14 to prevent further rotation of said screwed rod and to facilitate the detachment of the section of said screwed rod to the right of joint 23 by continued rotation of said driving tool. Said driving tool may now be withdrawn from the body of the patient leaving the device of the invention located as desired in its compressed condition and between the spinous processes of the adjacent vertebrae.

The device and the components thereof may be manufactured from any materials which have been shown to be suitable for implantation in the human body. Such materials may if desired be coated or otherwise treated to reduce inflammation and or promote healing of insertion wounds using materials and methods known to those skilled in the art of production of medical prostheses. If the device is manufactured wholly from non-metallic components radio opaque materials may be advantageously incorporated in some or all of the components in order to render the device or parts thereof visible under fluoroscopy during the procedure for implantation in the human body.

What we claim is:

1. A device for insertion between adjacent spinous processes of adjacent vertebrae comprising:
    a rod defining a longitudinal axis and having a threaded portion and an unthreaded portion, the rod adapted to be coupled to a driver;
    a first collar threadably coupled to the threaded portion of the rod;
    a second collar coupled to the unthreaded portion of the rod;
    a plurality of members pivotally coupled together so as to be movable between an extended condition and a compressed condition, with at least one of the plurality of members pivotally coupled to the first collar and at least one of the plurality of members pivotally coupled to the second collar such that the rotation of the rod moves the plurality of members between the extended condition and the compressed condition to support the adjacent spinous processes;
    a detachable portion that extends beyond the first collar when the plurality of members are in the compressed condition, the detachable portion operable to be removed by the driver; and
    a stop nut fixedly coupled to the threaded portion of the rod, the stop nut operable to engage a side of the first collar opposite the driver when the plurality of members is in the compressed condition to facilitate the removal of the detachable portion of the rod;
    wherein the threaded portion of the rod defines a threaded bore, and the detachable portion includes a threaded projection that engages the threaded bore of the threaded portion such that the rod has a uniform thread pattern, and the engagement of the stop nut with the first collar prevents the rotation of the rod so that further rotation of the driver removes the detachable portion from the threaded portion of the rod.

2. The device of claim 1, wherein the members of the plurality are symmetric about the longitudinal axis.

3. The device of claim 2, wherein the plurality of members includes about ten members and the plurality of members further comprises:
    a first one of the plurality of members pivotally coupled to the first collar to extend in a first direction;
    a second one of the plurality of members pivotally coupled to the first collar to extend in a second direction;
    a third one of the plurality of members pivotally coupled to the second collar to extend in a third direction;
    a fourth one of the plurality of members pivotally coupled to the second collar to extend in a fourth direction; and
    wherein three of the plurality of members pivotally couple the first one of the plurality of members to the third one of the plurality of members, and three of the plurality of members pivotally couple the second one of the plurality of members to the fourth one of the plurality of members.

4. The device of claim 3, wherein the plurality of members are pivotally coupled to each other at a pivot point by a cylindrical pin having concentric sections of different diameters sized to be received within apertures formed adjacent to an end of each of the plurality of members.

5. The device of claim 4, further comprising:
    a plurality of wire springs, with one of the plurality of wire springs coupled at each pivot point to apply tension the plurality of members in both the extended and compressed conditions.

6. The device of claim 3, wherein the three plurality of members that pivotally couple the first one of the plurality of members to the third one of the plurality of members define a substantially U-shaped configuration in the compressed condition to support the adjacent spinous process, and the three of the plurality of members that pivotally couple the second one of the plurality of members to the fourth one of the plurality of members define a substantially U-shaped configuration in the compressed condition to support the adjacent spinous process.

7. The device of claim 3, wherein the first one of the plurality of members and the second one of the plurality of members are pivotally coupled to the first collar by short projections that extend outwardly from the first collar to engage bores formed adjacent to an end of the first one of the plurality of members and the second one of the plurality of members, and the third one of the plurality of members and the fourth one of the plurality of members are pivotally coupled to the second collar by short projections that extend outwardly from the second collar to engage bores formed adjacent to an end of the third one of the plurality of members and the fourth one of the plurality of members.

8. The device of claim 1, wherein the second collar is slidably coupled to the rod so that rotation of the rod moves the first collar relative to the second collar.

9. The device of claim 8, wherein the rod further comprises a terminating cap that prevents the rod from being withdrawn through the second collar.

10. The device of claim 1, wherein in the extended condition, at least two of the plurality of members are generally parallel to the longitudinal axis of the rod, and in the compressed condition, at least two of the members of the plurality are generally perpendicular to the longitudinal axis of the rod.

11. The device of claim 1, wherein the threaded portion of the rod further comprises a shaped portion at a proximal end that mates with the driver.

12. The device of claim 1, in combination with a driver operable to rotate the rod to move the plurality of members from the extended condition to the compressed condition.

* * * * *

UNITED STATES PATENT AND TRADEMARK OFFICE
CERTIFICATE OF CORRECTION

| | | |
|---|---|---|
| PATENT NO. | : 8,323,344 B2 | |
| APPLICATION NO. | : 12/294357 | |
| DATED | : December 4, 2012 | |
| INVENTOR(S) | : Geoffrey Harrison Galley et al. | |

It is certified that error appears in the above-identified patent and that said Letters Patent is hereby corrected as shown below:

Col. 3, line 12 -- "canula" should be --cannula--.
Col. 3, line 29 -- "and or" should be --and/or--.
Col. 4, line 35 -- After "tension" insert --to--.

Signed and Sealed this
Twelfth Day of March, 2013

Teresa Stanek Rea
*Acting Director of the United States Patent and Trademark Office*